United States Patent
Wu et al.

(10) Patent No.: US 12,061,181 B2
(45) Date of Patent: Aug. 13, 2024

(54) METHOD AND APPARATUS FOR MEASURING WOOD DENSITY OF LIVE TIMBER

(71) Applicant: AEROSPACE INFORMATION RESEARCH INSTITUTE, CHINESE ACADEMY OF SCIENCES, Beijing (CN)

(72) Inventors: Bingfang Wu, Beijing (CN); Fangming Wu, Beijing (CN)

(73) Assignee: AEROSPACE INFORMATION RESEARCH INSTITUTE, CHINESE ACADEMY OF SCIENCES, Beijing (CN)

( * ) Notice: Subject to any disclaimer, the term of this patent is extended or adjusted under 35 U.S.C. 154(b) by 358 days.

(21) Appl. No.: 17/621,844

(22) PCT Filed: Oct. 28, 2019

(86) PCT No.: PCT/CN2019/113686
§ 371 (c)(1),
(2) Date: Dec. 22, 2021

(87) PCT Pub. No.: WO2021/072801
PCT Pub. Date: Apr. 22, 2021

(65) Prior Publication Data
US 2022/0326207 A1    Oct. 13, 2022

(30) Foreign Application Priority Data
Oct. 16, 2019    (CN) ......................... 201910982349.2

(51) Int. Cl.
*G01N 9/24*    (2006.01)
*G01N 9/36*    (2006.01)
(Continued)

(52) U.S. Cl.
CPC ........... *G01N 33/0098* (2013.01); *G01N 9/24* (2013.01); *G01N 9/36* (2013.01); *H04B 1/0475* (2013.01)

(58) Field of Classification Search
CPC ........ G01N 33/0098; G01N 9/24; G01N 9/36; G01N 2291/0238; G01N 33/46;
(Continued)

(56) References Cited

U.S. PATENT DOCUMENTS 5,524,771 A    6/1996    Kairi et al.
7,057,743 B2    6/2006    Merkel et al.
(Continued)

FOREIGN PATENT DOCUMENTS

CN    1032238 A    4/1989
CN    101231280 A    7/2008
(Continued)

OTHER PUBLICATIONS

International Search Report (including English translation) and Written Opinion for International Application No. PCT/CN2019/113686, dated Jun. 24, 2020, 11 pages.
(Continued)

*Primary Examiner* — Robert R Raevis
(74) *Attorney, Agent, or Firm* — Westman, Champlin & Koehler, P.A.

(57) ABSTRACT

A method and an apparatus were disclosed for measuring wood density of live timber. The method comprising: measuring a diameter of a test part of the live timber at a first height from a ground surface; transmitting and receiving microwave in a preset frequency range in air at a first distance greater than the diameter, measuring a first ratio of a transmitted microwave signal to a first received microwave signal at different frequencies; transmitting microwave in the air at the first height and microwave penetrates the test
(Continued)

part, receiving the microwave at the first distance from the microwave transmitting position, measuring a second ratio of a transmitted microwave signal to a second received microwave signal at different frequencies, calculating a dielectric constant and an attenuation constant; calculating the wood density according to a relationship between the wood density and the dielectric constant and the attenuation constant.

13 Claims, 7 Drawing Sheets

(51) Int. Cl.
  *G01N 33/00* (2006.01)
  *H04B 1/04* (2006.01)
(58) Field of Classification Search
  CPC ...... G01N 22/00; G01N 22/04; H04B 1/0475; G01R 27/2623; G01R 29/0892
  USPC ............... 73/32 R, 78; 250/306, 307, 336.1, 250/358.1–360.1, 395
  See application file for complete search history.

(56) References Cited

U.S. PATENT DOCUMENTS

| | | | |
|---|---|---|---|
| 7,280,227 | B2 | 10/2007 | Merkel et al. |
| 2003/0024315 | A1 | 2/2003 | Merkel et al. |
| 2003/0146767 | A1* | 8/2003 | Steele ................. G01N 9/24 324/640 |
| 2003/0218468 | A1 | 11/2003 | Holmes |
| 2006/0098211 | A1 | 5/2006 | Merkel et al. |
| 2017/0074711 | A1 | 3/2017 | Chung et al. |

FOREIGN PATENT DOCUMENTS

| | | |
|---|---|---|
| CN | 102384766 A | 3/2012 |
| CN | 102735580 A | 10/2012 |
| CN | 105466956 A | 4/2016 |
| CN | 106442635 A | 2/2017 |
| CN | 107192635 A | 9/2017 |
| JP | 2003315285 A | 11/2003 |
| WO | 0214847 A1 | 2/2002 |
| WO | 0218920 A1 | 3/2002 |
| WO | 2014070057 A1 | 5/2014 |
| WO | 2018127434 A1 | 7/2018 |

OTHER PUBLICATIONS

First Office Action, including Search Report, for Chinese Patent Application No. 201910982349.2, dated Jul. 3, 2020, 20 pages.

Extended European Search Report for European Application No. 19949004.6, dated Jun. 19, 2023, 12 pages.

Baath L B et al., "Microwave Polarimetry Tomography of Wood", IEEE Sensors Journal, IEEE, USA, vol. 5, No. 2, Apr. 1, 2005 (Apr. 1, 2005), pp. 209-215, XP011128742.

Wu Fang-Ming, "Research Progress of Microwave Nondestructive Testing Technology for Standing Trees", Forestry Machinery & Woodworking Equipment, vol. 46, No. 12, Dec. 1, 2018 (Dec. 1, 2018), pp. 9-14, XP055803262.

Effendi Mohhammad Ridwan et al., "Back Propagation Technique for Image Reconstruction of Microwave Tomography", Proceedings of The 2019 9th International Conference on Biomedical Engineering and Technology, Mar. 28, 2019 (Mar. 28, 2019), pp. 186-189, XP093049981.

Salvade A et al., "A New Microwave Axial Tomograph for the Inspection of Dielectric Materials", IEEE Transations on Instrumentation and Measurement, IEEE, USA, vol. 57, No. 7, Jul. 1, 2009 (Jul. 1, 2009), pp. 2072-2079, XP011256201.

* cited by examiner

METHOD AND APPARATUS FOR MEASURING WOOD DENSITY OF LIVE TIMBER

CROSS-REFERENCE TO RELATED APPLICATION

This application is a 371 National Stage Application of International Application No. PCT/CN2019/113686, filed on Oct. 28, 2019, which published as WO/2021/072801 A1, filed on Apr. 22, 2021, not in English, which claims priority to the Chinese Patent Application No. 201910982349.2, filed on Oct. 16, 2019 and is entitled "method and apparatus for measuring wood density of live timber", the contents of which are incorporated herein by reference in their entireties.

BACKGROUND OF THE DISCLOSURE

Field of Technology

The present disclosure relates to the technical field of measuring, in particular to a method and apparatus for measuring wood density of live timber.

Description of the Related Art

Wood density is an important physical property of live timber, which is closely related to mechanical properties of live timber, such as elastic modulus, bending resistance and compression resistance, and wood utilization. It is an important index to evaluate characteristics of wood such as quality, grade, strength and so on, it is a common index to study a correlation between a symbolic utilization of live timber and the cultivation of live timber, and it is also a basic quantity of biomass measurement in ecosystem research.

In related technologies, some researchers sample live timber, measure volume and mass of a sample respectively, and obtain the wood density of live timber by use of a ratio of mass to volume. Some researchers sample live timber, pulverize a sample into wood powder and scan and collect near-infrared spectroscopy with a Fourier transform spectrometer, and measure basic wood density or green wood density of the sample by use of an obtained rapid measurement model. Although traditional weighing method is simple in principle, easy to practice, and high in accuracy of estimation results, it needs to sample according to standards and make test pieces of standard volume, it is labor-intensive and takes a long time, and it is necessary to take samples directly from raw materials, so that measurement time is long, which is not conducive to on-site testing. As for near-infrared spectroscopy method, the near-infrared spectroscopy of samples from different sections of trees have a large difference, which has a greater impact on the prediction accuracy, in addition, a thickness of the sample also has an impact on the prediction accuracy, resulting in a relatively large error in measured wood density.

Some researchers use Pilodyn method to detect the wood density of live timber, a working principle of this method include: injecting a probe with a certain diameter into the live timber with a preset energy, and predicting the wood density of live timber according to a correlation between a penetration depth of the probe and properties of live timber. This method has advantages of rapid determination and less damage to live timber. However, the disadvantage is that the penetration depth of the probe is limited, for the live timber with a large diameter, the probe only stays at a sapwood part of the live timber. Therefore, this method has a better predictive effect on an outside density of the live timber, and an entire radial density prediction is not ideal. In addition, a bark has a greater impact on the test, and sometimes it is necessary to peel off the bark for testing to get a more ideal result, which will bring new wounds to the live timber.

SUMMARY

In order to overcome problems of long time-consuming, damage to live timber and large errors in measured wood density in related technology of method for measuring wood density of live timber, embodiments of the present disclosure provide a method and an apparatus for measuring wood density of live timber, which reduces the time-consuming and damage to the live timber, increases a density measurement range of an entire radial direction of the live timber, so that improving accuracy of the measured wood density.

According to an aspect of the present disclosure, a method for measuring wood density of live timber is provided and comprising:

measuring a diameter of a test part of the live timber at a first height from a ground surface;

transmitting and receiving microwave in a preset frequency range in air at a first distance greater than the diameter, and measuring a first ratio of a transmitted microwave signal to a first received microwave signal at different frequencies;

transmitting microwave in the air at the first height so that microwave penetrates the test part of the live timber, receiving the microwave at the first distance from the microwave transmitting position, and measuring a second ratio of a transmitted microwave signal to a second received microwave signal at different frequencies;

calculating a dielectric constant and an attenuation constant of the live timber according to the first ratio, the second ratio and the diameter;

determining a relationship between the wood density of the live timber and the dielectric constant and the attenuation constant, and calculating the wood density of the live timber according to the relationship.

Optionally, further comprises:

measuring the second ratio multiple times in different directions of the test part of the live timber;

calculating the dielectric constant and the attenuation constant of the test part of the live timber in different directions respectively according to the first ratio, the second ratio of multiple measurements, and the diameter;

calculating the wood density of the live timber in different directions respectively at the test part according to the relationship;

calculating an average value of the wood density of the test part of the live timber in different directions to obtain an average wood density of the test part of the live timber.

Optionally, calculating the dielectric constant and the attenuation constant of the live timber according to the first ratio, the second ratio of multiple measurements, and the diameter comprises:

calculating a first time domain data and a second time domain data corresponding to the first ratio and the second ratio by using an inverse Fourier transform;

calculating transmission time and amplitude attenuation of microwave at the test part of the live timber according to the first time domain data and the second time domain data;

calculating the dielectric constant of the live timber according to the transmission time and the diameter; and calculating the attenuation constant of the live timber according to the amplitude attenuation and the diameter.

Optionally, calculating transmission time and amplitude attenuation of microwave at the test part of the live timber according to the first time domain data and the second time domain data comprises:

selecting a maximum value of an amplitude of a waveform of the first time domain data to determine a first time and a first amplitude corresponding to the maximum value of the amplitude;

selecting a maximum value of an amplitude of a waveform of the second time domain data to determine a second time and a second amplitude corresponding to the maximum value of the amplitude;

calculating the transmission time according to the first time, the second time, and the diameter;

calculating the amplitude attenuation according to the first amplitude and the second amplitude.

Optionally, the relationship between the wood density of the live timber and the dielectric constant and the attenuation constant comprises:

$$\rho = \frac{a\varepsilon + b}{1 - \frac{\alpha - q}{100p}}$$

wherein, $\rho$ is the wood density of the live timber, $\varepsilon$ is the dielectric constant of the live timber, $\alpha$ is the attenuation constant of the live timber, and a, b, p, q are pre-calibrated parameters related to tree species of the live timber.

According to another aspect of the present disclosure, an apparatus for measuring wood density of live timber is provided and comprising:

a transmitter, configured to generate and transmit microwave signal in a preset frequency range according to a control signal;

a receiver, configured to receive a first received microwave signal after a first distance propagated in air at a first distance greater than a diameter of a test part of the live timber from the transmitter, and orthogonally demodulate the first received microwave signal and a transmitted microwave signal to convert the first received microwave signal into a first baseband signal and a second baseband signal, the receiver is further configured to receive a second received microwave signal penetrating the test part of the live timber, and orthogonally demodulate the second received microwave signal and the transmitted microwave signal to convert the second received microwave signal into a third baseband signal and a fourth baseband signal;

a controller connected to the transmitter and the receiver, configured to provide the control signal to the transmitter, collect and store the first baseband signal, the second baseband signal, the third baseband signal and the fourth baseband signal, and calculate the wood density according to the transmitted microwave signal, the first baseband signal, the second baseband signal, the third baseband signal and the fourth baseband signal;

a touch screen, configured to set parameters, send user instructions to the controller and display a calculation result of the controller;

a communication interface module, configured to obtain relevant parameters in a relationship between the wood density of the live timber and a dielectric constant and an attenuation constant from a server, and send the parameters set by the touch screen, the relevant parameters and the calculation result of the controller to the server;

a reference clock module, configured to generate a clock reference for the controller and the transmitter; and a voltage converter, configured to alter a voltage of an input power to provide various types of secondary power required.

Optionally, the receiver comprises: a pre-selection filter, a pre-amplifier, a PI-type attenuator, a post-amplifier, a quadrature demodulator, a low-pass filter and an analog-to-digital converter, the pre-selection filter is configured to filter out interference signals in the first received microwave signal and the second received microwave signal;

the pre-amplifier and the post-amplifier are configured to amplify the first received microwave signal and the second received microwave signal after preselection and filtering;

the PI-type attenuator is configured to adjust an amplification gain of the entire receiving link;

the quadrature demodulator is configured to orthogonally demodulate the first received microwave signal output by the post-amplifier and the transmitted microwave signal to obtain the first baseband signal and the second baseband signal of the first received microwave signal, the quadrature demodulator is further configured to orthogonally demodulate the second received microwave signal output by the post-amplifier and the transmitted microwave signal to obtain the third baseband signal and the fourth baseband signal of the second received microwave signal;

the low-pass filter is configured to filter out interference high-frequency signals of the first baseband signal, the second baseband signal, the third baseband signal and the fourth baseband signal;

the analog-to-digital converter is configured to convert the first baseband signal, the second baseband signal, the third baseband signal and the fourth baseband signal into a first digital signal a second digital signal, a third digital signal and a fourth digital signal respectively.

Optionally, the controller comprises: a data collection module, a data storage module, a data processing module, a system control module and a data transmission module, the data collection module is configured to control the analog-to-digital converter to collect the first digital signal and the second digital signal of the first received microwave signal, and the third digital signal and the fourth digital signal of the second received microwave signal;

the data storage module is configured to store the first digital signal, the second digital signal, the third digital signal and the fourth digital signal, the relevant parameters in the relationship between the wood density of the live timber and the dielectric constant and the attenuation constant, and the diameter;

the data processing module is configured to calculate a first ratio of the transmitted microwave signal to the first received microwave signal at different frequencies according to the first digital signal and the second digital signal, the data processing module is further configured to calculate a second ratio of the transmitted microwave signal to the second received microwave signal at different frequencies according to the third digital signal and the fourth digital signal, the data processing module is further configured to calculate the wood density of the live timber by using calculation formulas of the dielectric constant and the attenuation constant, and the relationship between the wood density of the live timber and the dielectric constant and the attenuation constant, according to the first ratio, the second ratio, the diameter and the relevant parameters;

the system control module is configured to receive the parameters set by the touch screen, the user instructions, and/or the calculation result of the data processing module, and transmit the control signal to the transmitter, or send the calculation result to the communication interface module;

the data transmission module is configured to provide data paths between various modules of the controller.

According to another aspect of the present disclosure, a computer-readable storage medium is provided, which stores computer instructions, and when the computer instructions are executed, the above method for measuring wood density of live timber is performed.

According to another aspect of the present disclosure, a computer program product is provided and comprising a computer program, the computer program comprises program instructions, and when the program instructions are executed by a mobile terminal, cause the mobile terminal to perform operations comprising the above method for measuring wood density of live timber.

The embodiments of the present disclosure have the following advantages or beneficial effects:

(1) The measured wood density process of the embodiment of the present disclosure is simple, and there is no need to sample and make standard-volume test pieces according to a standard, thus saving manpower, material resources and time-consuming, and there is no need to take samples from the live timber, which realizes Non-destructive measurement of live timber, convenient for on-site measurement. The relevant parameters in the relational for calculating the wood density are obtained through pre-tests, and they have passed tests and meet a measurement accuracy. Therefore, the obtained wood density also meets the measurement accuracy, which ensures the measurement accuracy of the embodiment of the present disclosure. The microwave may penetrate the test part of the live timber to measure the wood density in entire radial direction, which improves the measurement range of the whole radial wood density of the live timber and improves the accuracy of the measured wood density.

(2) Measure the wood density of the test part of the live timber from different directions, calculate the average of the wood density of the test part of the live timber in different directions, and obtain an average wood density of the test part of the live timber. Since microwaves may penetrate the test part of the live timber from different directions, the wood density of whole radial direction of the test part may be measured from different directions, and the average value of the wood density of the test part of the live timber in different directions may be calculated, and further improve the accuracy of the measured wood density.

BRIEF DESCRIPTION OF THE DRAWINGS

Through the following description of the embodiments of the present disclosure with reference to the accompanying drawings, the above and other objectives, features, and advantages of the present disclosure will be more apparent, in the accompanying drawings.

DETAILED DESCRIPTION OF THE DISCLOSURE

The present disclosure will be described below based on examples, but the present disclosure is not limited to these examples. In the following detailed description of the present disclosure, some specific details are described in detail. Those skilled in the art can fully understand the present disclosure without the description of these details. In order to avoid obscuring the essence of the present disclosure, the well-known methods, processes, and procedures are not described in detail. In addition, the drawings are not necessarily drawn to scale.

The present disclosure uses a microwave method to measure a wood density of standing timber, and a measurement mechanism includes: a dielectric constant of wood is a physical parameter that characterizes a polarization of the wood under an action of an alternating electric field and an ability of a dielectric to store charges. The dielectric constant of wood is affected by wood moisture content, wood density, microwave frequency, tree species and other factors. When the wood density increases, in fact, a volume percentage of substance of a cell wall increases. As the volume percentage of the substance increases, the number of dipoles per unit volume of wood increases, which enhances a polarization reaction of the wood, so the wood's dielectric constant increases accordingly.

The attenuation constant is one of transmission constants, which represents an attenuation of an amplitude or power of electromagnetic waves or electrical signals during transmission. When a microwave penetrates a live timber, its amplitude will be attenuated due to reflection, absorption and scattering of the live timber, which is characterized as the attenuation constant. Therefore, when the dielectric constant and the attenuation constant are related to the wood density, the wood density may be obtained through the dielectric constant and the attenuation constant.

Figure 1:
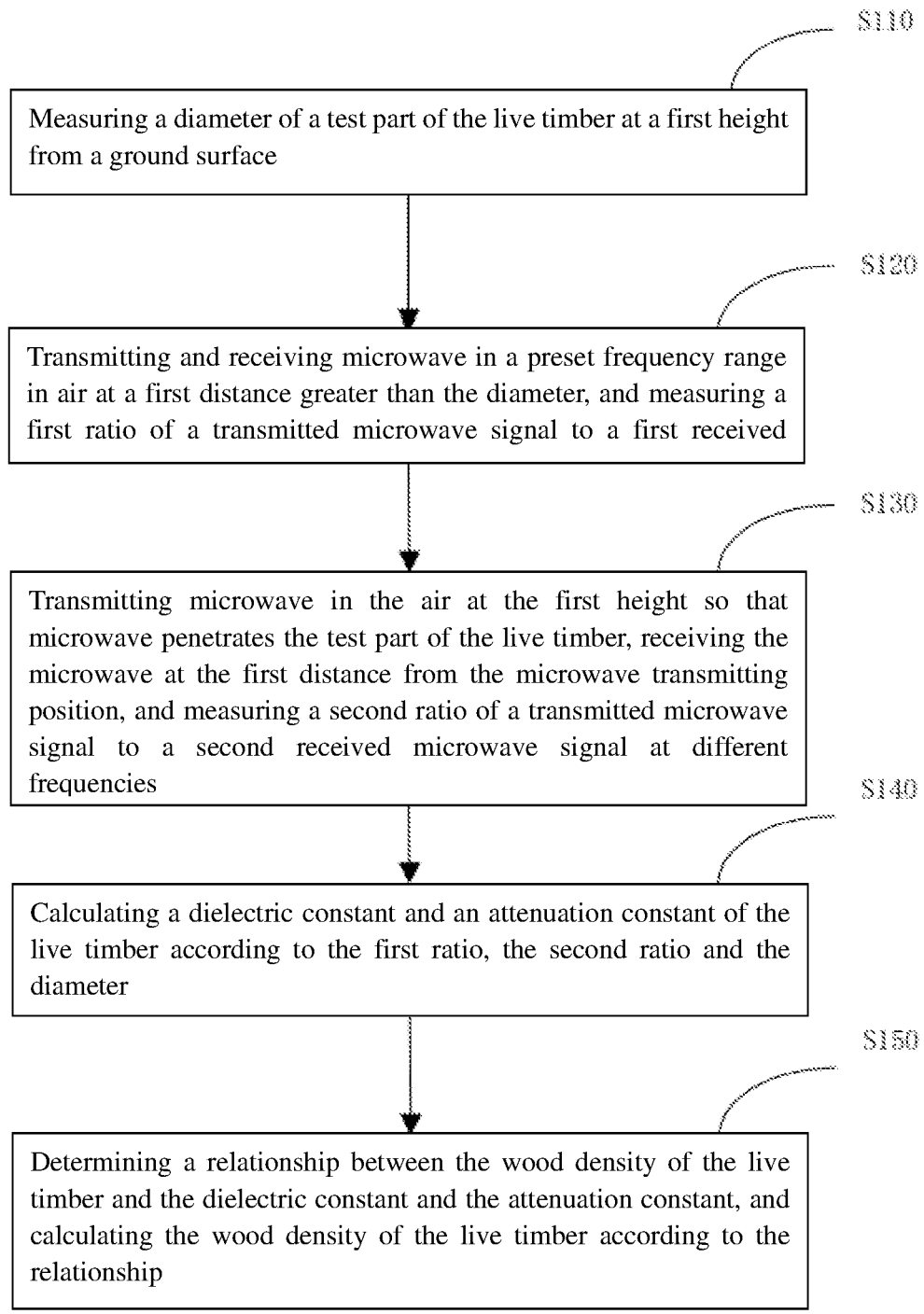
FIG. 1 shows a schematic flow chart of a method for measuring wood density of live timber according to an embodiment of the present disclosure.

FIG. 1 shows a schematic flow chart of a method for measuring wood density of live timber according to an embodiment of the present disclosure. Specifically, including steps described below.

In step S110, measuring a diameter of a test part of the live timber at a first height from a ground surface.

In this step, for the live timber to be measured, measuring the diameter of the test part of the live timber at the first height from the ground surface. The first height is, for example, a breast height position of the live timber, and a corresponding diameter is a breast diameter of the live timber.

In step S120, transmitting and receiving microwave in a preset frequency range in air at a first distance greater than the diameter, and measuring a first ratio of a transmitted microwave signal to a first received microwave signal at different frequencies.

In this step, transmitting the microwave in the preset frequency range in the air, the microwave in the preset frequency range is a microwave band which is compatible with a wood density of the live timber to be measured, that is, the microwave band that is most sensitive to the density of the live timber to be measured, for example, 2 GHz to 8 GHz. Receiving microwave in the preset frequency range at a position separated by the first distance from a microwave transmitting position, and measuring the first ratio $H_0(\omega)$ of the transmitted microwave signal $X(\omega)$ to the first received microwave signal $Y_0(\omega)$ at different frequencies $\omega$. The first distance D is greater than the diameter d. Optionally, a height of a transmitting position and a receiving position of the microwave from the ground surface is the first height H.

In step S130, transmitting microwave in the air at the first height so that microwave penetrates the test part of the live timber, receiving the microwave at the first distance from the microwave transmitting position, and measuring a second ratio of a transmitted microwave signal to a second received microwave signal at different frequencies.

Figure 2:
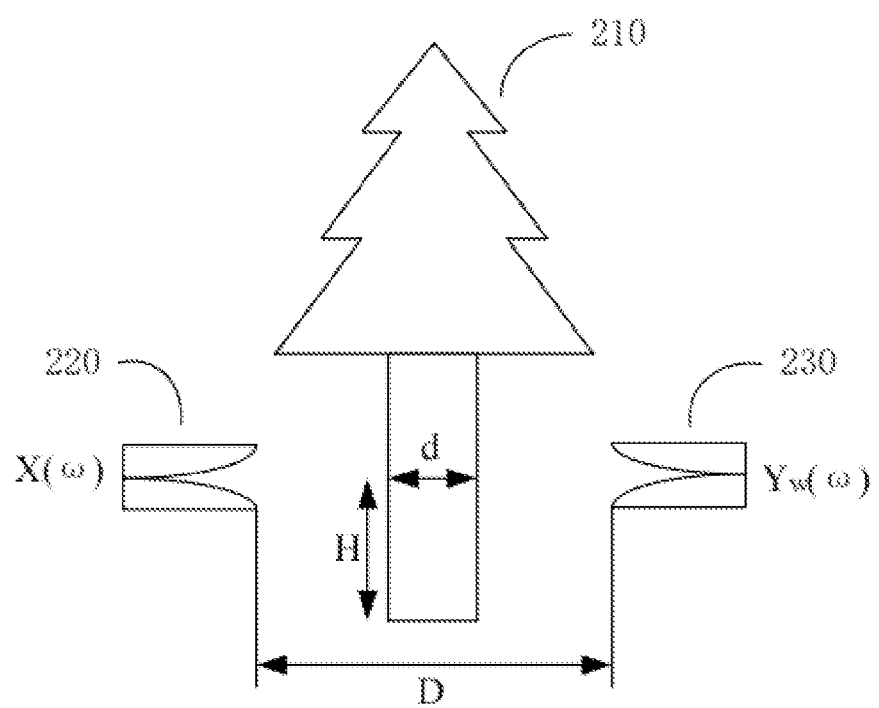
FIG. 2 shows an application scene diagram of the method for measuring wood density of live timber according to an embodiment of the present disclosure.

FIG. 2 shows an application scene diagram of the method for measuring wood density of live timber according to an embodiment of the present disclosure. As shown in FIG. 2, the live timber to be measured 210 is located between a transmitting end 220 and a receiving end 230 of the microwave in the preset frequency range, and the microwave is transmitted by the transmitting end 220 and penetrates through the test part of the live timber 210 to the receiving end 230. The transmitting end 220 and the receiving end 230 are separated by the first distance D, the test part of the live timber 210 is a first height H from the ground surface, and the diameter of the test part of the live timber 210 at the corresponding first height is d.

In this step, in the application scene shown in FIG. 2, transmitting microwave in the air at the first height H so that microwave penetrates the test part of the live timber 210, receiving the microwave at the first distance D (the receiving end 230) from the microwave transmitting position (the transmitting end 220), and measuring a second ratio $H_w(\omega)$ of a transmitted microwave signal $X(\omega)$ to a second received microwave signal $Y_w(\omega)$ at different frequencies $\omega$.

In step S140, calculating a dielectric constant and an attenuation constant of the live timber according to the first ratio, the second ratio and the diameter.

In this step, calculating the dielectric constant $\varepsilon$ and the attenuation constant $\alpha$ of the live timber according to the first ratio $H_0(\omega)$, the second ratio $H_w(\omega)$ and the diameter d.

Specifically, the step includes: calculating a first time domain data $h_0(t)$ and a second time domain data $h_w(t)$ corresponding to the first ratio $H_0(\omega)$ and the second ratio $H_w(\omega)$ by using an inverse Fourier transform.

Figure 3:
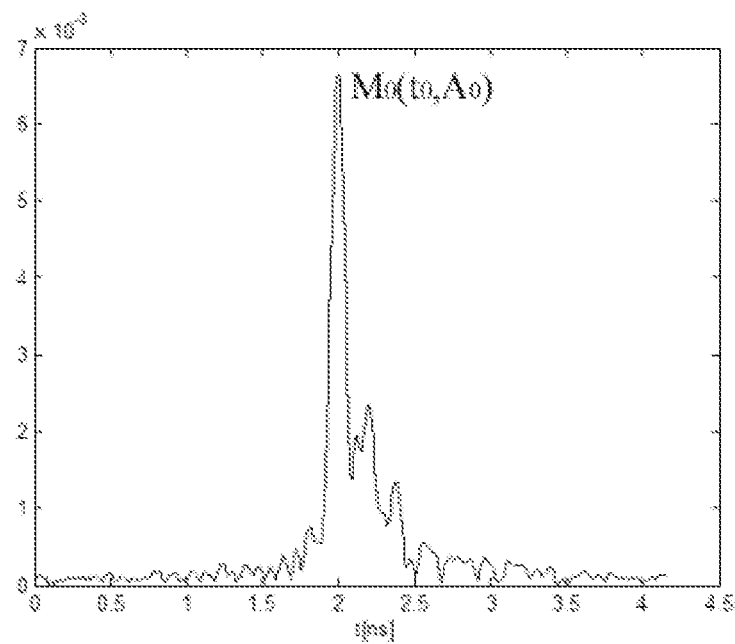
FIG. 3 shows a waveform diagram of time domain data transmitted by microwave in air according to an embodiment of the present disclosure.
Figure 4:
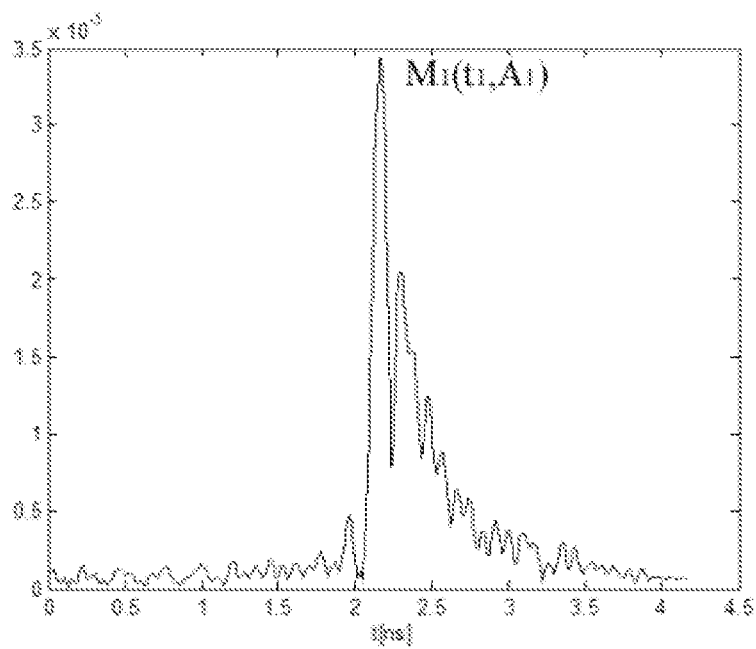
FIG. 4 shows a waveform diagram of time domain data transmitted by microwave in the live timber and the air according to an embodiment of the present disclosure.

Calculating transmission time $\Delta t$ and amplitude attenuation $\Delta A$ of the microwave at the test part of the live timber according to the first time domain data $h_0(t)$ and the second time domain data $h_w(t)$. FIG. 3 shows a waveform diagram of time domain data transmitted by microwave in air according to an embodiment of the present disclosure, specifically, shows the waveform of the first time domain data $h_0(t)$. As shown in FIG. 3, an ordinate of the first time domain data $h_0(t)$ is the amplitude value, an abscissa is time, and a maximum value of the amplitude of the waveform of the first time domain data $h_0(t)$ is the point $M_0(t_0, A_0)$. FIG. 4 shows a waveform diagram of time domain data transmitted by microwave in the live timber and the air according to an embodiment of the present disclosure, specifically, shows the waveform of the second time domain data $h_w(t)$ corresponding to the second ratio $H_w(\omega)$ of the measured transmitted microwave signal $X(\omega)$ to the second received microwave signal $Y_w(\omega)$ when the live timber to be measured is fragrant cedar, the diameter d of the test part which is 130 cm from the ground surface is 13.3 cm, and the first distance D between the transmitting end 220 and the receiving end 230 of the microwave is 30 cm. As shown in FIG. 4, an ordinate of the second time domain data $h_w(t)$ is the amplitude value, an abscissa is time, and a maximum value of the amplitude of the waveform of the second time domain data $h_w(t)$ is the point $M_1(t_1, A_1)$.

Figure 5:
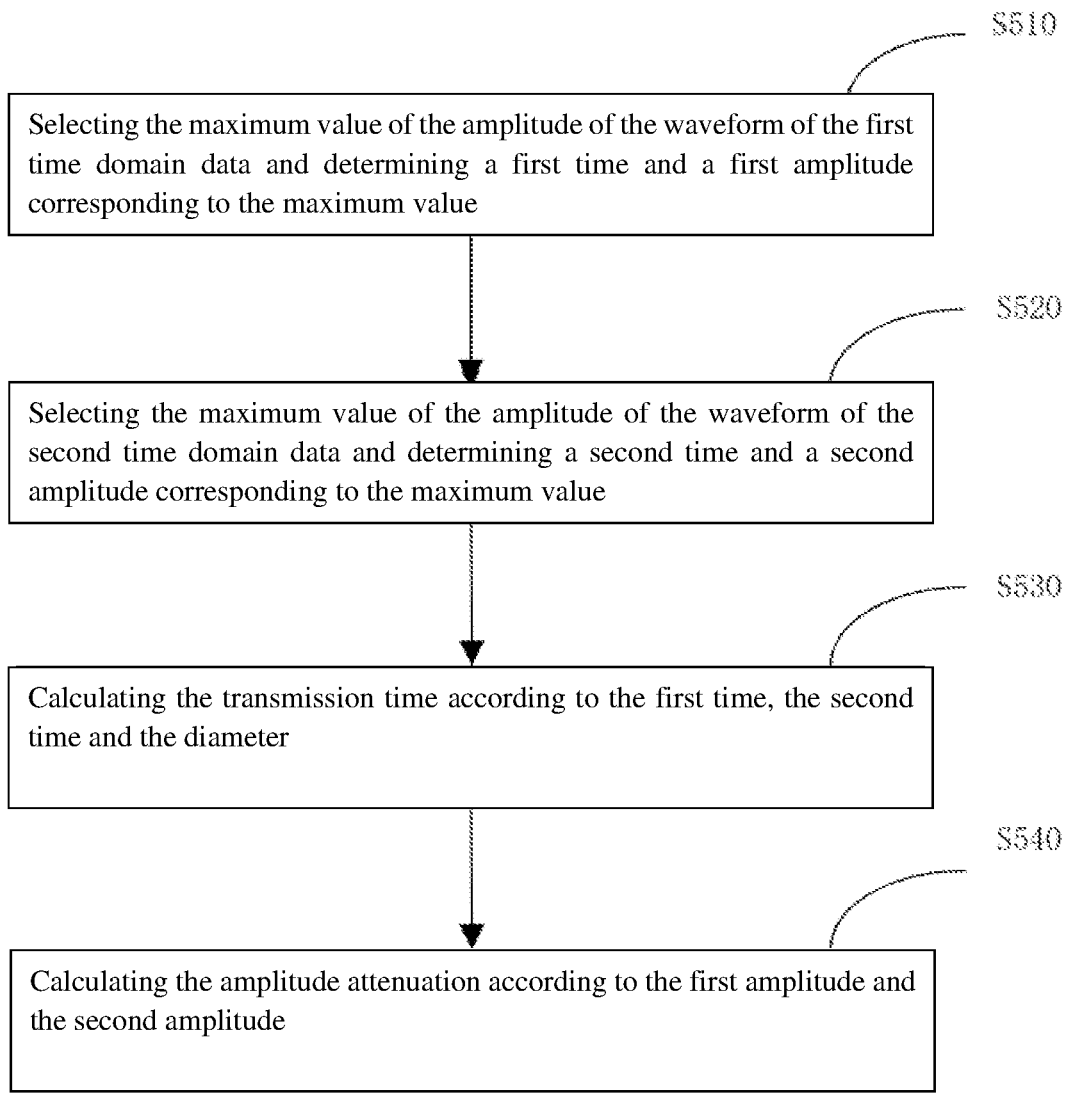
FIG. 5 shows a schematic flow chart of a method for measuring transmission time and amplitude attenuation of microwaves at a test part of the live timber according to an embodiment of the present disclosure.

FIG. 5 shows a schematic flow chart of a method for measuring transmission time and amplitude attenuation of microwaves at a test part of the live timber according to an embodiment of the present disclosure. Specifically, including steps described below.

In step S510, selecting the maximum value $M_0(t_0, A_0)$ of the amplitude of the waveform of the first time domain data $h_0(t)$ as shown in FIG. 3, and determining a first time $t_0$ and a first amplitude $A_0$ corresponding to the maximum value $M_0(t_0, A_0)$.

In step S520, selecting the maximum value $M_1(t_1, A_1)$ of the amplitude of the waveform of the second time domain data $h_w(t)$ as shown in FIG. 4, and determining a second time $t_1$ and a second amplitude $A_1$ corresponding to the maximum value $M_1(t_1, A_1)$.

In step S530, calculating the transmission time $\Delta t$ according to the first time $t_0$, the second time $t_1$ and the diameter d. A formula for calculating the transmission time of the microwave at the test part of the live timber is:

$$\Delta t = t_1 - t_0 + d/c \quad (1)$$

Wherein, $\Delta t$ is the transmission time of the microwave in the test part of the live timber, $t_1$ is the second time corresponding to the maximum value $M_1(t_1, A_1)$ of the amplitude of the waveform of the second time domain data $h_w(t)$ transmitted by the microwave in the standing wood and the air, $t_0$ is the first time corresponding to the maximum value $M_0(t_0, A_0)$ of the amplitude of the waveform of the first time domain data $h_0(t)$ transmitted by the microwave in the air, d is the diameter of the test part at the first height H of the live timber from the ground surface, and c is a propagation speed of the microwave in the air.

In step S540, calculating the amplitude attenuation $\Delta A$ according to the first amplitude $A_0$ and the second amplitude $A_1$. A formula for calculating the amplitude attenuation $\Delta A$ of the microwave transmission in the test part in the live timber is:

$$\Delta A = -20 lg(A_1/A_0) \quad (2)$$

Wherein, $\Delta A$ is the amplitude attenuation of the microwave transmission in the test part of the live timber, $A_1$ is the second amplitude corresponding to the maximum value $M_1(t_1, A_1)$ of the amplitude of the waveform of the second time domain data $h_w(t)$ transmitted by the microwave in the standing wood and the air, and $A_0$ is the second amplitude corresponding to the maximum value $M_0$ ($t_0$, $A_0$) of the amplitude of the waveform of the first time domain data $h_0$ (t) transmitted by the microwave in the air.

Calculating the dielectric constant ε of the live timber according to the transmission time Δt and diameter d. A formula for calculating the dielectric constant ε of the live timber corresponding to the microwave in the preset frequency range is:

$$\varepsilon = (\Delta t c/d)^2 \quad (3)$$

Wherein, ε is the dielectric constant of the live timber, Δt is the transmission time of the microwave in the test part of the live timber, d is the diameter of the test part at the first height H of the live timber from the ground surface, and c is the propagation speed of the microwave in the air.

Calculating the attenuation constant α of the standing timber according to the amplitude attenuation ΔA and diameter d. A formula for the attenuation constant α of the live timber corresponding to the microwave in the preset frequency range is:

$$\alpha = \Delta A/(8.686d) \quad (4)$$

Wherein, α is the attenuation constant of the standing timber, ΔA is the amplitude attenuation of the microwave transmission in the test part of the live timber, and d is the diameter of the test part at the first height H of the live timber from the ground surface.

In step S150, determining a relationship between the wood density of the live timber and the dielectric constant and the attenuation constant, and calculating the wood density of the live timber according to the relationship.

Figure 6:
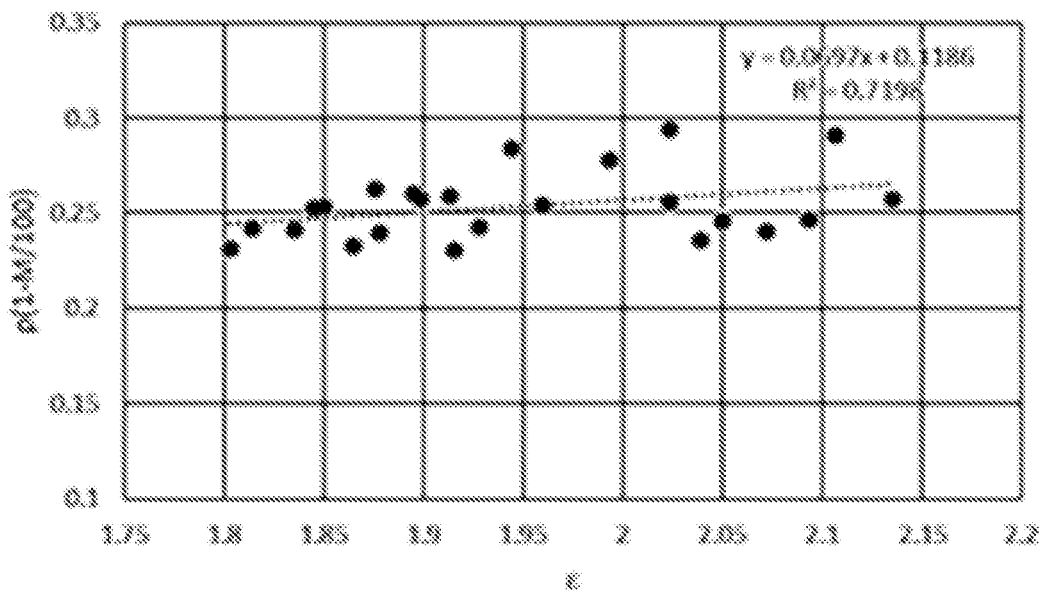
FIG. 6 shows a relationship between wood density, moisture and dielectric constant of live timber according to an embodiment of the present disclosure.

The dielectric constant of wood is not a constant value, factors that affect the dielectric constant of wood are usually include wood moisture content, wood density, microwave frequency and tree species etc. FIG. 6 shows a relationship between wood density, moisture and dielectric constant of live timber according to an embodiment of the present disclosure, specifically, the live timber to be measured is *Cunninghamia lanceolata* (Lamb.) Hook. As shown in FIG. 6, an abscissa is the dielectric constant ε of the live timber corresponding to the microwave in the preset frequency range, and an ordinate is the wood density of the live timber. Multiple test points in the figure correspond to different moisture, the relationship between the density, the moisture and the dielectric constant of *Cunninghamia lanceolata* (Lamb.) Hook. may be obtained from the figure as a linear relationship.

In this step, according to the relationship between the density, the moisture and the dielectric constant of the live timber shown in FIG. 6 and a relationship between the moisture and the attenuation constant, a relationship between wood density, the dielectric constant and the attenuation constant of live timber can be deduced as:

$$\rho = \frac{a\varepsilon + b}{1 - \frac{\alpha - q}{100p}} \quad (5)$$

wherein, ρ is the wood density of the live timber, ε is the dielectric constant of the live timber, α is the attenuation constant of the live timber, and a, b, p, q are pre-calibrated parameters related to tree species of the live timber. The tree species refer to the species, tree parts, tree age, and growing area of the live timber.

Figure 7:
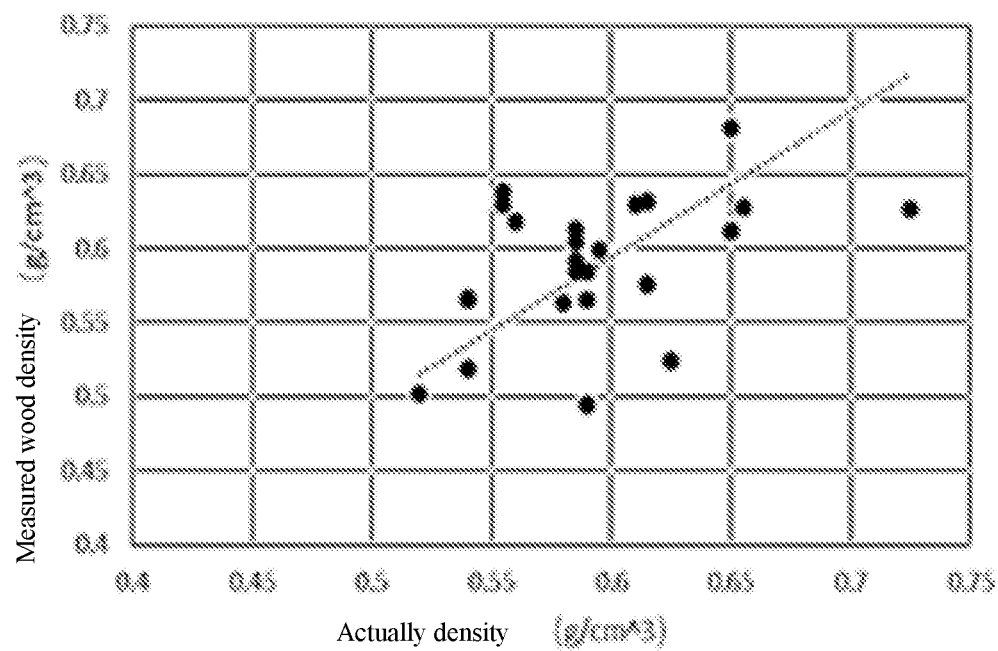
FIG. 7 shows a comparison diagram of a measured density and an actual density of the wood density of the live timber according to an embodiment of the present disclosure.

FIG. 7 shows a comparison diagram of a measured density and an actual density of the wood density of the live timber according to an embodiment of the present disclosure. According to the method for measuring the wood density of live timber in the embodiment of the present disclosure, the wood density is measured multiple times. As shown in FIG. 7, an average error of the measured wood density of the live timber and an actual density of the live timber is 0.03.

According to the embodiment of the present disclosure, for the live timber to be measured, measuring the diameter of the test part of the live timber at the first height from the ground surface; transmitting and receiving microwave in the preset frequency range in air at the first distance greater than the diameter, and measuring the first ratio of the transmitted microwave signal to the first received microwave signal at different frequencies; transmitting microwave in the air at the first height so that microwave penetrates the test part of the live timber, receiving the microwave at the first distance from the microwave transmitting position, and measuring the second ratio of the transmitted microwave signal to the second received microwave signal at different frequencies; calculating the dielectric constant and the attenuation constant of the live timber according to the first ratio, the second ratio and the diameter; determining the relationship between the wood density of the live timber and the dielectric constant and the attenuation constant, and calculating the wood density of the live timber according to the relationship. The measured wood density process of the embodiment of the present disclosure is simple, and there is no need to sample and make standard-volume test pieces according to a standard, thus saving manpower, material resources and time-consuming, and there is no need to take samples from the live timber, which realizes Non-destructive measurement of live timber, convenient for on-site measurement. The relevant parameters in the relational for calculating the wood density are obtained through pre-tests, and they have passed tests and meet a measurement accuracy. Therefore, the obtained wood density also meets the measurement accuracy, which ensures the measurement accuracy of the embodiment of the present disclosure. The microwave may penetrate the test part of the live timber to measure the wood density in entire radial direction, which improves the measurement range of the whole radial wood density of the live timber and improves the accuracy of the measured wood density.

In some embodiments of the present disclosure, step S120 to step S150 are repeated, measuring the second ratio multiple times in different directions of the test part of the live timber; calculating the dielectric constant and the attenuation constant of the test part of the live timber in different directions respectively according to the first ratio, the second ratio of multiple measurements, and the diameter; calculating the wood density of the live timber in different directions respectively at the test part according to the relationship; calculating an average value of the wood density of the test part of the live timber in different directions to obtain an average wood density of the test part of the live timber. Since microwaves may penetrate the test part of the live timber from different directions, the wood density of whole radial direction of the test part may be measured from different directions, and the average value of the wood density of the test part of the live timber in different directions may be calculated, and further improve the accuracy of the measured wood density.

Figure 8:
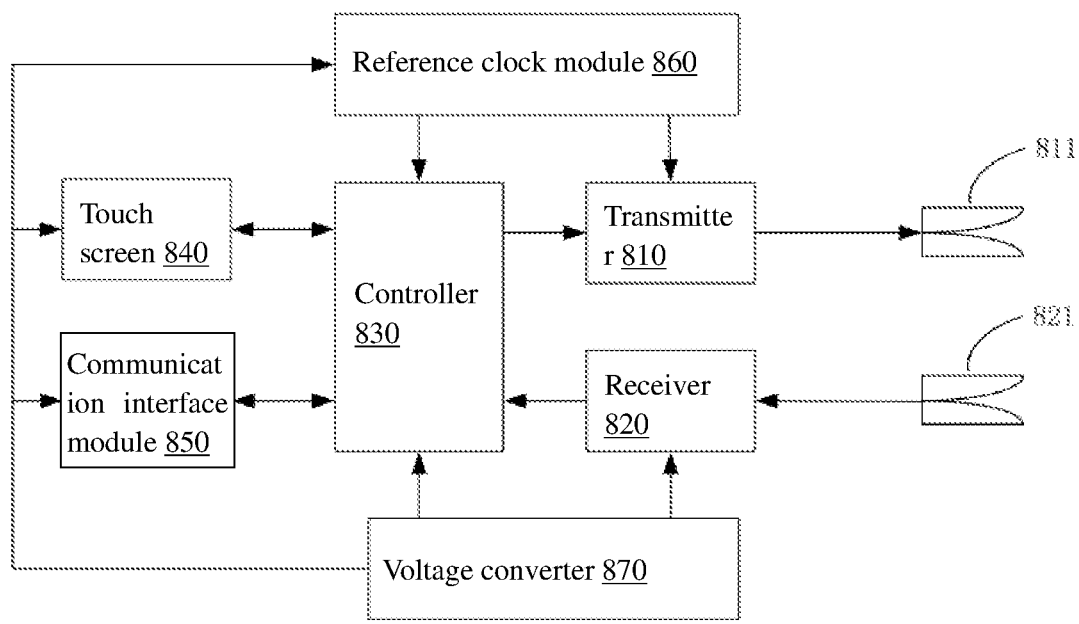
FIG. 8 shows a block diagram of an apparatus for measuring the wood density of live timber according to an embodiment of the present disclosure.

FIG. 8 shows a block diagram of an apparatus for measuring the wood density of live timber according to an embodiment of the present disclosure. As shown in FIG. 8, the apparatus for measuring the wood density of the live timber includes: a transmitter 810, a receiver 820, a controller 830, a touch screen 840, a communication interface module 850, a reference clock module 860, and a voltage converter 870. The transmitter 810 includes a transmitting antenna 811, and the receiver 820 includes a receiving antenna 821.

The transmitter 810 mainly includes a phase-locked loop frequency synthesizer, a power divider, and a power amplifier, and is configured to generate frequency stepping microwaves with a certain power according to a control signal, and transmit microwave signal in a preset frequency range.

The receiver 820 is configured to receive a first received microwave signal after a first distance propagated in air at a first distance greater than a diameter of a test part of the live timber from the transmitter 810, and orthogonally demodulate the first received microwave signal and a transmitted microwave signal to convert the first received microwave signal into a first baseband signal and a second baseband signal, and then extract amplitude and phase information, receive a second received microwave signal penetrating the test part of the live timber, and orthogonally demodulate the second received microwave signal and the transmitted microwave signal to convert the second received microwave signal into a third baseband signal and a fourth baseband signal, and then extract amplitude and phase information.

The transmitting antenna 811 of the transmitter 810 and the receiving antenna 821 of the receiver 820 both employs broadband directional antennas. The transmitting antenna 811 and the receiving antenna 821 are respectively connected to the transmitter 810 and the receiver 820 through a cable assembly. The transmitting antenna 811 transmits microwave signals to an object to be measured, and the receiving antenna 821 receives the first received microwave signal and the second received microwave signal.

The controller 830 is connected to the transmitter 810 and the receiver 820, and is configured to provide the control signal including a trigger signal and a timing control signal to the transmitter 810, collect and store the first baseband signal, the second baseband signal, the third baseband signal and the fourth baseband signal, and calculate the wood density of the live timber according to the transmitted microwave signal, the first baseband signal, the second baseband signal, the third baseband signal and the fourth baseband signal. In some embodiments, the controller 830 is further configured to provide the trigger signal and the timing control signal to the receiver 820. In some embodiments, the controller 830 is further configured to transmit data to a server.

The touch screen 840 is configured to set parameters, send user instructions to the controller 830 and display a calculation result of the controller 830.

The communication interface module 850 is configured to realize a data interaction between the controller 830 and the server, and obtain relevant parameters in a relationship (Formula (5)) between the wood density of the live timber and a dielectric constant and an attenuation constant from a server, and send the calculation result of the controller to the serve.

The reference clock module 860 configured to generate clock references for the controller 860 and the transmitter 810.

The voltage converter 870 is configured to voltage converter an input power to provide various types of secondary power required by functional modules and devices in the apparatus for measuring the wood density of live timber. The wood density measurement of live timber is carried out in a field, the wood density measurement device of live timber is powered by a lithium battery. The voltage converter 870 further has a power management function and may switch between lithium battery power supply and input power supply.

Figure 9:
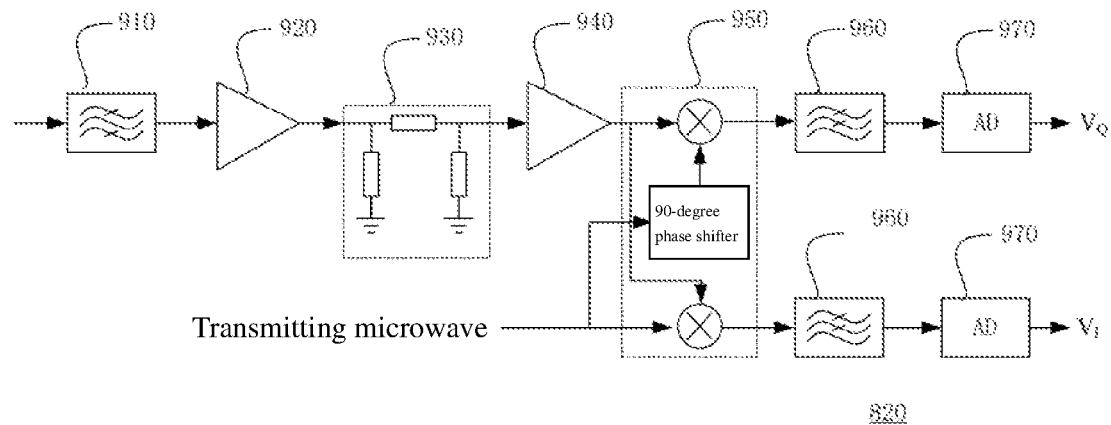
FIG. 9 shows a block diagram of a receiver according to an embodiment of the present disclosure.

FIG. 9 shows a block diagram of a receiver according to an embodiment of the present disclosure. As shown in FIG. 9, considering that the density and water content of different live timbers vary widely, the receiver 820 includes: a pre-selection filter 910, a pre-amplifier 920, a PI-type attenuator 930, a post-amplifier 940, a quadrature demodulator 950, a low-pass filter 960 and an analog-to-digital converter 970. The pre-amplifier 920, the PI-type attenuator 930, and the post-amplifier 940 in the receiver 820 adopt two-stage amplification and one-stage PI-type attenuator to complete a front-end amplification of a frequency signal.

The pre-selection filter 910 is configured to filter out interference signals in the first received microwave signal and the second received microwave signal.

The pre-amplifier 920 and the post-amplifier 940 are configured to amplify the first received microwave signal and the second received microwave signal after preselection and filtering.

The pi-type attenuator 930 is configured to adjust an amplification gain of the entire receiving link to ensure that all devices in the receiver 820 work in a linear region.

The quadrature demodulator 950 is configured to orthogonally demodulate the first received microwave signal output by the post-amplifier 940 and the transmitted microwave signal to obtain the first baseband signal and the second baseband signal of the first received microwave signal, and orthogonally demodulate the second received microwave signal output by the post-amplifier 940 and the transmitted microwave signal to obtain the third baseband signal and the fourth baseband signal of the second received microwave signal, so that extract amplitude and phase information of the first received microwave signal and the second received microwave signal.

The first baseband signal and the second baseband signal are a set of orthogonal signals, and the phase difference between the first baseband signal and the second baseband signal is 90 degrees. For example, the first baseband signal is an I baseband signal, and the second baseband signal is a Q baseband signal. The third baseband signal and the fourth baseband signal are a set of orthogonal signals, and the phase difference between the third baseband signal and the fourth baseband signal is 90 degrees. For example, the third baseband signal is the I baseband signal, and the fourth baseband signal is the Q baseband signal.

The low-pass filter 960 is configured to filter out interference high-frequency signals of the first baseband signal, the second baseband signal, the third baseband signal and the fourth baseband signal.

The analog-to-digital converter 970 is configured to convert the first baseband signal, the second baseband signal, the third baseband signal and the fourth baseband signal into a first digital signal a second digital signal, a third digital signal and a fourth digital signal respectively. For example, the first digital signal is I digital signal, the second digital signal is Q digital signal, the third digital signal is I digital signal, and the fourth digital signal is Q digital signal.

The I baseband signal and the Q baseband signal are vectors. Therefore, a amplitude attenuation and phase shift of the first received microwave signal and the amplitude attenuation and phase shift of the second received microwave signal may be calculated using a triangle identity equation as follows:

$$\tau = \sqrt{V_I^2 + V_Q^2} \quad (6)$$

Wherein, τ is the amplitude attenuation of the first received microwave signal or the second received microwave signal, $V_I$ is the I digital signal of the first received microwave signal or the second received microwave signal, and $V_Q$ is the Q digital signal of the first received microwave signal or the second received microwave signal.

$$\varphi = \tan^{-1}\frac{V_Q}{V_I} \quad (7)$$

Wherein, φ is the phase shift of the first received microwave signal or the second received microwave signal, $V_I$ is the I digital signal of the first received microwave signal or the second received microwave signal, and $V_Q$ is the Q digital signal of the first received microwave signal or the second received microwave signal.

Figure 10:
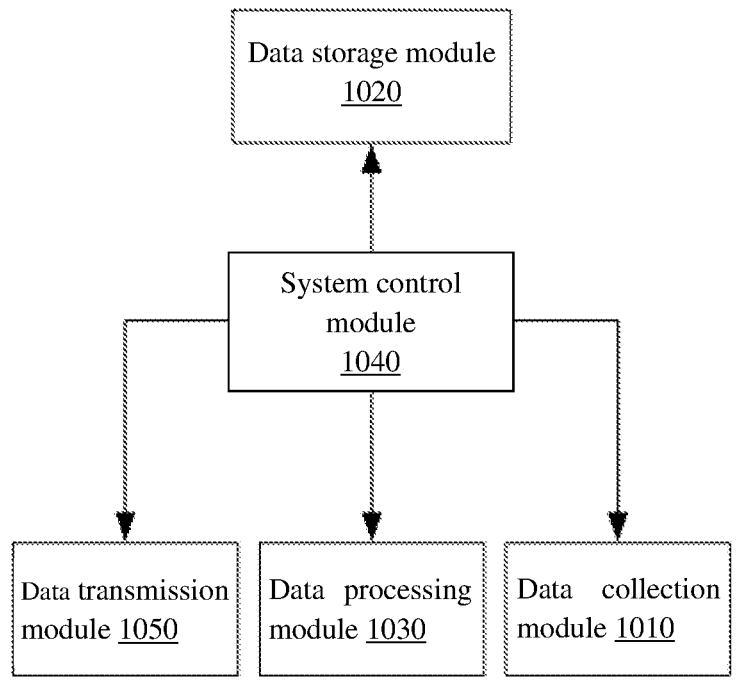
FIG. 10 shows a block diagram of a controller according to an embodiment of the present disclosure.

FIG. 10 shows a block diagram of a controller according to an embodiment of the present disclosure. Considering that a control function of the apparatus for measuring the wood density of live timber has the characteristics of periodic repetition and parallel output requirements of the control signal, as shown in FIG. 10, Field-Programmable Gate Array (FPGA) is used to realize a logic control of the controller 830 in the measurement apparatus, to give full play to advantages of FPGA's high integration, low power consumption, etc. In addition, a programmable feature of FPGA facilitates an upgrade of the controller 830 in future. As shown in FIG. 10, the controller 830 includes: a data collection module 1010, a data storage module 1020, a data processing module 1030, a system control module 1040 and a data transmission module 1050.

The data collection module 1010 is configured to control the analog-to-digital converter 970 to collect the first digital signal and the second digital signal of the first received microwave signal, and the third digital signal and the fourth digital signal of the second received microwave signal.

The data storage module 1020 is configured to store the first digital signal, the second digital signal, the third digital signal and the fourth digital signal, the relevant parameters in the relationship (formula (5)) between the wood density of the live timber and the dielectric constant and the attenuation constant, and the diameter of the test part of the live timber.

The data processing module 1300 is configured to analyze the received digital signal, according to the first digital signal and the second digital signal stored in the data storage module 1020, use formulas (6) and (7) to calculate the amplitude attenuation and phase shift of the first received microwave signal. Calculate a first ratio of the frequency domain signal of the transmitted microwave to the frequency domain signal of the first received microwave is calculated according to the amplitude attenuation and phase shift of the first received microwave signal. According to the third digital signal and the fourth digital signal stored in the data storage module 1020, use formulas (6) and (7) to calculate the amplitude attenuation and phase shift of the second received microwave. Calculate a second ratio of the frequency domain signal of the transmitted microwave to the frequency domain signal of the second received microwave according to the amplitude attenuation and phase shift of the second received microwave.

The calculation formula for the first ratio of the transmitted microwave signal of different frequencies to the first received microwave signal and the second ratio of the transmitted microwave signal of different frequencies to the second received microwave signal is:

$$H(\omega) = \tau \angle \varphi \quad (8)$$

Wherein, H(ω) is the first ratio of the transmitted microwave signal of different frequencies ω to the first received microwave signal or the second ratio of the transmitted microwave signal of different frequencies ω to the second received microwave signal, φ is the phase shift of the first received microwave signal or the second received microwave signal, and τ is the amplitude attenuation of the first received microwave signal or the second received microwave signal.

According to the first ratio, the second ratio, the diameter and the related parameters (the related parameters in formula (5)), use the calculation formulas of dielectric constant and attenuation constant (formula (1) to formula (4)), the relationship (formula (5)) between the wood density of the live timber and the dielectric constant and the attenuation constant to calculate the wood density of the live timber.

The system control module 1040 is configured to receive the parameters set by the touch screen 840, the user instructions, and/or the calculation result of the data processing module 1030, and transmit the control signal to the transmitter 810, or send the calculation result to the communication interface module 850;

The data transmission module 1050 is configured to provide data paths between various modules of the controller 850.

Correspondingly, the embodiment of the present disclosure provides a computer-readable storage medium, which stores computer instructions, and when the computer instructions are executed, the above method for measuring wood density of live timber is performed.

Correspondingly, the embodiment of the present disclosure further provides a computer program product, comprising a computer program, the computer program comprises program instructions, and when the program instructions are executed by a mobile terminal, cause the mobile terminal to perform operations comprising the above method for measuring wood density of live timber.

The flowcharts and block diagrams in the drawings illustrate possible system frameworks, functions, and operations of the systems, methods, and devices of the embodiments of the present disclosure, the blocks on flowcharts and block diagrams can represent a module, program segment or just a piece of code, the modules, program segments, and codes are all executable instructions used to implement prescribed logic functions. It should also be noted that the executable instructions that implement the prescribed logic functions can be recombined to generate new modules and program segments. Therefore, the blocks and the sequence of the blocks in the drawings are only used to better illustrate the process and steps of the embodiment, and should not be used as a limitation to the disclosure itself.

The above are only some embodiments of the present disclosure and are not used to limit the present disclosure. For those skilled in the art, the present disclosure can have various modifications and changes. Any modification, equivalent replacement, improvement, etc. made within the spirit and principle of the present disclosure should be included in the protection scope of the present disclosure.

What is claimed is:

1. A method for measuring wood density of live timber, comprising:
   measuring a diameter of a test part of the live timber at a first height from a ground surface;
   transmitting microwave in a preset frequency range in air at a first distance greater than the diameter, by use of a transmitter, and measuring a first ratio of a transmitted microwave signal to a first received microwave signal at different frequencies, by use of a receiver;
   transmitting microwave in the air at the first height so that microwave penetrates the test part of the live timber, by use of the transmitter, receiving the microwave at the first distance from the microwave transmitting position, and measuring a second ratio of a transmitted microwave signal to a second received microwave signal at different frequencies, by use of the receiver;
   calculating a dielectric constant and an attenuation constant of the live timber according to the first ratio, the second ratio and the diameter, by use of a controller;
   determining a relationship between the wood density of the live timber and the dielectric constant and the attenuation constant, and calculating the wood density of the live timber according to the relationship, by use of the controller.

2. The method for measuring wood density of live timber according to claim 1, wherein,
   measuring a second ratio of a transmitted microwave signal to a second received microwave signal at different frequencies comprises:
   measuring the second ratio at least twice in different directions of the test part of the live timber;
   calculating a dielectric constant and an attenuation constant of the live timber according to the first ratio, the second ratio and the diameter comprises: calculating the dielectric constant and the attenuation constant of the test part of the live timber at least twice in different directions respectively according to the first ratio, the second ratio of multiple measurements, and the diameter;
   calculating the wood density of the live timber according to the relationship comprises:
   calculating the wood density of the live timber at least twice in different directions respectively at the test part according to the relationship;
   the method further comprises: calculating an average value of the wood density of the test part of the live timber in different directions to obtain an average wood density of the test part of the live timber.

3. The method for measuring wood density of live timber according to claim 2, wherein calculating the dielectric constant and the attenuation constant of the live timber according to the first ratio, the second ratio of multiple measurements, and the diameter comprises:
   calculating a first time domain data and a second time domain data corresponding to the first ratio and the second ratio by using an inverse Fourier transform;
   calculating transmission time and amplitude attenuation of microwave at the test part of the live timber according to the first time domain data and the second time domain data;
   calculating the dielectric constant of the live timber according to the transmission time and the diameter; and
   calculating the attenuation constant of the live timber according to the amplitude attenuation and the diameter.

4. The method for measuring wood density of live timber according to claim 3, wherein calculating transmission time and amplitude attenuation of microwave at the test part of the live timber according to the first time domain data and the second time domain data comprises:
   selecting a maximum value of an amplitude of a waveform of the first time domain data to determine a first time and a first amplitude corresponding to the maximum value of the amplitude;
   selecting a maximum value of an amplitude of a waveform of the second time domain data to determine a second time and a second amplitude corresponding to the maximum value of the amplitude;
   calculating the transmission time according to the first time, the second time, and the diameter;
   calculating the amplitude attenuation according to the first amplitude and the second amplitude.

5. The method for measuring wood density of live timber according to claim 1, wherein the relationship between the wood density of the live timber and the dielectric constant and the attenuation constant comprises:

$$\rho = \frac{a\varepsilon + b}{1 - \frac{\alpha - q}{100p}}$$

wherein, $\rho$ is the wood density of the live timber, $\varepsilon$ is the dielectric constant of the live timber, $\alpha$ is the attenuation constant of the live timber, and a, b, p, q are pre-calibrated parameters related to tree species of the live timber.

6. A apparatus for measuring wood density of live timber comprising:
   a transmitter, configured to generate and transmit microwave signal in a preset frequency range according to a control signal;
   a receiver, configured to receive a first received microwave signal after a first distance propagated in air at a first distance greater than a diameter of a test part of the live timber from the transmitter, and orthogonally demodulate the first received microwave signal and a transmitted microwave signal to convert the first received microwave signal into a first baseband signal and a second baseband signal,
   the receiver is further configured to receive a second received microwave signal penetrating the test part of the live timber, and orthogonally demodulate the second received microwave signal and the transmitted microwave signal to convert the second received microwave signal into a third baseband signal and a fourth baseband signal;
   a controller connected to the transmitter and the receiver, configured to provide the control signal to the transmitter, collect and store the first baseband signal, the second baseband signal, the third baseband signal and the fourth baseband signal, and calculate the wood density according to the transmitted microwave signal, the first baseband signal, the second baseband signal, the third baseband signal and the fourth baseband signal;
   a touch screen, configured to set parameters, send user instructions to the controller and display a calculation result of the controller;
   a communication interface module, configured to obtain relevant parameters in a relationship between the wood density of the live timber and a dielectric constant and an attenuation constant from a server, and send the parameters set by the touch screen, the relevant parameters and the calculation result of the controller to the server ;
a reference clock module, configured to generate a clock reference for the controller and the transmitter; and
a voltage converter connected to the controller and the receiver, configured to alter a voltage of an input power to provide various types of secondary power required by the controller and the receiver.

7. The apparatus for measuring wood density of live timber according to claim 6, wherein the receiver comprises: a pre-selection filter, a pre-amplifier, a PI-type attenuator, a post-amplifier, a quadrature demodulator, a low-pass filter and an analog-to-digital converter,
the pre-selection filter is configured to filter out interference signals in the first received microwave signal and the second received microwave signal;
the pre-amplifier and the post-amplifier are configured to amplify the first received microwave signal and the second received microwave signal after preselection and filtering;
the PI-type attenuator is configured to adjust an amplification gain of the entire receiving link;
the quadrature demodulator is configured to orthogonally demodulate the first received microwave signal output by the post-amplifier and the transmitted microwave signal to obtain the first baseband signal and the second baseband signal of the first received microwave signal,
the quadrature demodulator is further configured to orthogonally demodulate the second received microwave signal output by the post-amplifier and the transmitted microwave signal to obtain the third baseband signal and the fourth baseband signal of the second received microwave signal;
the low-pass filter is configured to filter out interference high-frequency signals of the first baseband signal, the second baseband signal, the third baseband signal and the fourth baseband signal;
the analog-to-digital converter is configured to convert the first baseband signal, the second baseband signal, the third baseband signal and the fourth baseband signal into a first digital signal a second digital signal, a third digital signal and a fourth digital signal respectively.

8. The apparatus for measuring wood density of live timber according to claim 7, wherein the controller comprises: a data collection module, a data storage module, a data processing module, a system control module and a data transmission module,
the data collection module is configured to control the analog-to-digital converter to collect the first digital signal and the second digital signal of the first received microwave signal, and the third digital signal and the fourth digital signal of the second received microwave signal;
the data storage module is configured to store the first digital signal, the second digital signal, the third digital signal and the fourth digital signal, the relevant parameters in the relationship between the wood density of the live timber and the dielectric constant and the attenuation constant, and the diameter;
the data processing module is configured to calculate a first ratio of the transmitted microwave signal to the first received microwave signal at different frequencies according to the first digital signal and the second digital signal,
the data processing module is further configured to calculate a second ratio of the transmitted microwave signal to the second received microwave signal at different frequencies according to the third digital signal and the fourth digital signal,
the data processing module is further configured to calculate the wood density of the live timber by using calculation formulas of the dielectric constant and the attenuation constant, and the relationship between the wood density of the live timber and the dielectric constant and the attenuation constant, according to the first ratio, the second ratio, the diameter and the relevant parameters;
the system control module is configured to receive the parameters set by the touch screen, the user instructions, and/or the calculation result of the data processing module, and transmit the control signal to the transmitter, or send the calculation result to the communication interface module;
the data transmission module is configured to provide data paths between various modules of the controller.

9. A computer-readable storage medium storing computer instructions, which when executed, cause a device to:
measure a diameter of a test part of the live timber at a first height from a ground surface;
transmit microwave in a preset frequency range in air at a first distance greater than the diameter, and measure a first ratio of a transmitted microwave signal to a first received microwave signal at different frequencies;
transmit microwave in the air at the first height so that microwave penetrates the test part of the live timber, receive the microwave at the first distance from the microwave transmitting position, and measure a second ratio of a transmitted microwave signal to a second received microwave signal at different frequencies;
calculate a dielectric constant and an attenuation constant of the live timber according to the first ratio, the second ratio and the diameter;
determine a relationship between the wood density of the live timber and the dielectric constant and the attenuation constant, and calculate the wood density of the live timber according to the relationship.

10. The computer-readable storage medium to claim 9, wherein,
measuring a second ratio of a transmitted microwave signal to a second received microwave signal at different frequencies comprises: measuring the second ratio at least twice in different directions of the test part of the live timber;
calculating a dielectric constant and an attenuation constant of the live timber according to the first ratio, the second ratio and the diameter comprises: calculating the dielectric constant and the attenuation constant of the test part of the live timber at least twice in different directions respectively according to the first ratio, the second ratio of multiple measurements, and the diameter;
calculating the wood density of the live timber according to the relationship comprises:
calculating the wood density of the live timber at least twice in different directions respectively at the test part according to the relationship;
the computer instructions which, when executed, further cause the device to calculate an average value of the wood density of the test part of the live timber in different directions to obtain an average wood density of the test part of the live timber.

11. The computer-readable storage medium to claim 10, wherein calculating the dielectric constant and the attenuation constant of the live timber according to the first ratio, the second ratio of multiple measurements, and the diameter comprises:
   calculating a first time domain data and a second time domain data corresponding to the first ratio and the second ratio by using an inverse Fourier transform;
   calculating transmission time and amplitude attenuation of microwave at the test part of the live timber according to the first time domain data and the second time domain data;
   calculating the dielectric constant of the live timber according to the transmission time and the diameter; and
   calculating the attenuation constant of the live timber according to the amplitude attenuation and the diameter.

12. The computer-readable storage medium to claim 11, wherein calculating transmission time and amplitude attenuation of microwave at the test part of the live timber according to the first time domain data and the second time domain data comprises:
   selecting a maximum value of an amplitude of a waveform of the first time domain data to determine a first time and a first amplitude corresponding to the maximum value of the amplitude;
   selecting a maximum value of an amplitude of a waveform of the second time domain data to determine a second time and a second amplitude corresponding to the maximum value of the amplitude;
   calculating the transmission time according to the first time, the second time, and the diameter;
   calculating the amplitude attenuation according to the first amplitude and the second amplitude.

13. The computer-readable storage medium to claim 9, wherein the relationship between the wood density of the live timber and the dielectric constant and the attenuation constant comprises:

$$\rho = \frac{\alpha \varepsilon + b}{1 - \frac{\alpha - q}{100p}}$$

wherein, $\rho$ is the wood density of the live timber, $\varepsilon$ is the dielectric constant of the live timber, $\alpha$ is the attenuation constant of the live timber, and a, b, p, q are pre-calibrated parameters related to tree species of the live timber.

* * * * *